United States Patent [19]

Fleet

[11] Patent Number: 5,026,870

[45] Date of Patent: Jun. 25, 1991

[54] METHOD OF PREPARING BICYCLIC TETRAHYDROXYLATED PYRROLIZIDINES

[75] Inventor: George W. J. Fleet, Oxford, United Kingdom

[73] Assignee: Monsanto Company, St. Louis, Mo.

[21] Appl. No.: 587,144

[22] Filed: Sep. 24, 1990

Related U.S. Application Data

[62] Division of Ser. No. 404,800, Sep. 8, 1989, Pat. No. 4,992,460.

[51] Int. Cl.$^5$ ............................................. C07D 487/10
[52] U.S. Cl. ..................................................... 548/453
[58] Field of Search ........................................ 548/453

[56] References Cited

PUBLICATIONS

Bruce et al., Chem. Abstract, vol. 113, No. 41154y (1990).
Collin et al., Chem. Abstract, vol. 113, No. 231743n (1990).
Bruce et al., Chem. Abstract, vol. 113, No. 97946a (1990).
Fleet et al., J. Chem. Soc., Perkin Trans. 1, 665–666 (1989).
Bashyal et al., Tetrahedron 43, 3083–3093 (1987).
Fleet et al., Tetrahedron 43, 979–990 (1987).
Fleet et al., Tetrahedron Lett., 26, 3127–3131 (1985).
Molyneux et al., Arch. Biochem. Biophys., 251, 450–457 (1986).
Raymond & Vogel, Tetrahedron Lett., 30, 705–706 (1989).
Setoi et al., Tetrahedron Lett. 26, 4617–4620 (1985).
Hamana et al., J. Org. Chem., 52, 5492–5494 (1987).
Fleet et al., Tetrahedron Lett., 29, 3603–3606 (1988).
Fleet et al., Tetrahedron Lett., 29, 5441–5445 (1988).
Anzeveno et al., J. Org. Chem. 54, 25392542 (1989).
Brimacombe and Tucker, Carbohydr. Res. 2, 341–348 (1966).
Stork et al., J. Am. Chem. Soc. 100, 8272–8273 (1978).

*Primary Examiner*—Mukund J. Shah
*Assistant Examiner*—Philip J. Datlow
*Attorney, Agent, or Firm*—Scott J. Meyer; James W. Williams, Jr.

[57] ABSTRACT

Novel bicyclic tetrahydroxylated pyrrolizidines are disclosed which are inhibitors of glycosidase enzymes. A preferred inhibitor is 1α,2α,6α,7α,7αβ-1,2,6-7-tetrahydroxypyrrolizidine. It is synthesized from D-glycero-D-gulo-heptono-1,4-lactone.

1 Claim, No Drawings

METHOD OF PREPARING BICYCLIC TETRAHYDROXYLATED PYRROLIZIDINES

This is a division of application Ser. No. 07/404,800, filed Sept. 8, 1989, now U.S. Pat. No. 4,992,460.

BACKGROUND OF THE INVENTION

This invention relates to novel bicyclic tetrahydroxylated pyrrolizidines and methods for their chemical synthesis. These compounds are useful inhibitors of glycosidase enzymes.

Several naturally occurring polyhydroxylated pyrrolidines, pyrrolizidines and indolizidines are powerful and specific inhibitors of glycosidases [Fellows and Fleet, Alkaloidal Glycosidase Inhibitors from Plants, in Natural Products Isolation (Ed. G. H. Wagman and R. Cooper), Elsevier, Amsterdam, 1988, pp. 540–560; Evans et al, *Phytochemistry*, 24 1953–1956 (1985)]. In recent years, plagiarism of plant chemistry has led to the synthesis of powerful inhibitors of other glycosidases [Fleet et al, *J. Chem. Soc., Perkin Trans.* 1, 665–666, (1989); Bashyal et al, *Tetrahedron* 43, 3083–3093 (1987), and Fleet et al, *Tetrahedron* 43, 979–990 (1987)]. It is now clear that, although changes in stereochemistry of the hydroxyl groups have profound effects on the selectivity of glycosidase inhibition, it is not easy to predict the effects of such changes [Fleet et al, *Tetrahedron Lett.*, 26 3127–3131 (1985)]. For example, 6-episcastanospermine (2) is a glucosidase inhibitor even though the stereochemistry of the four adjacent chiral centres in the piperidine is similar to those in the pyranose form of mannose [Molyneux et al, Arch. Biochem. Biophys., 251, 450–457 (1986)]. Similarly, 1,7a-diepialexine (3), structurally very similar to the powerful mannosidase inhibitor swainsonine (4), is an inhibitor of fungal glucan 1,4-α-glucosidase [Nash et al, *Phytochemistry*, submitted for publication]. Also, β-C-methyl deoxymannojirimycin (5) is a strong and specific α-L-fucosidase inhibitor and has no effect on human liver α-mannosidase [Fleet et al, *Tetrahedron Lett.*, 30, In Press (1989)].

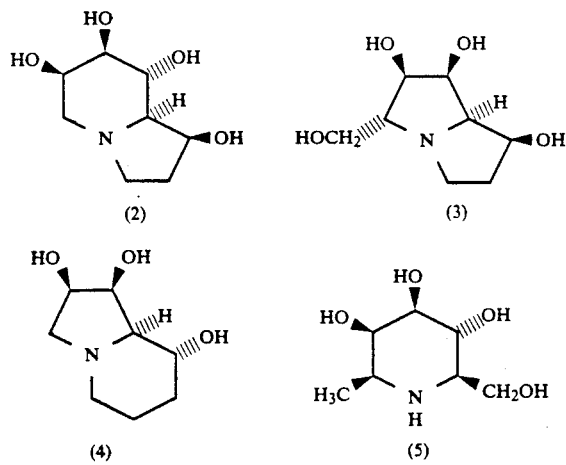

With a few exceptions [Raymond and Vogel, *Tetrahedron Lett.*, 30 705–706 (1989)], sugars have been the starting materials used in the synthesis of such compounds as castanospermines [such as (2)], Setoi et al, *Tetrahedron Lett.*, 26 4617–4620 (1985), Hamana et al, *J. Org. Chem.*, 52, 5492–5494 (1987) and Fleet et al, *Tetrahedron Lett.*, 29, 3603–3606 (1988); alexines [such as (3)], Fleet et al, *Tetrahedron Lett.*, 29, 5441–5445 (1988); and homonojirimycins [such as (4)], Anzeveno et al, *J. Org. Chem.* 54, 2539–2542 (1989). Invariably in the syntheses of these compounds with five adjacent chiral centres and six or seven adjacent functional groups, the strategy chosen has been to start from a hexose and to introduce the additional chiral centre late in the synthesis. An alternative is to start from derivatives of heptoses, that is by very early introduction of the additional chiral centre.

Relatively few studies have been reported on the protecting group chemistry of even readily available heptonolactones [Brimacombe and Tucker, *Carbohydr. Res.* 2, 341–348 (1966)]. Likewise, only a few examples of syntheses from heptose derivatives have been reported. One neat example is described by Stork et al, *J. Am. Chem. Soc.* 100, 8272–8273 (1978). Recently, a research group led by co-inventor Fleet herein has found that suitably protected heptonolactones can be powerful and readily manipulatable chiral pool materials. See Bruce et al, *Tetrahedron* 45, In press 1989, and copending application Ser. No. 07/352,068, filed May 15, 1989 now abandoned.

BRIEF DESCRIPTION OF THE INVENTION

In accordance with the present invention, novel bicyclic tetrahydroxylated pyrrolizidines are synthesized from the readily available heptonolactones, D-glycero-D-gulo-heptono-1,4-lactone and the analogous D-glycero-D-talo-heptono-1,4-lactone.

In a preferred embodiment of the invention, the novel 1α,2α,6α,7α,7aβ-1,2,6,7-tetrahydroxypyrrolizidine (1) is prepared from D-glycero-D-gulo-heptone-1,4-lactone by two different synthetic routes. This novel tetrahydroxylated pyrrolizidine is an effective inhibitor of human liver glycosidases.

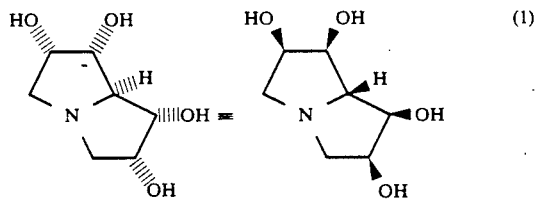

The tetrahydroxypyrrolizidone (1) is an analogue of 1,8-diepiswainsonine. A similar analogue of swainsonine can be made by analogous methods starting with D-glycero-D-talo-heptono-1,4-lactone to produce the novel (1S, 2R, 6R, 7S)-1,2,6,7-tetrahydroxypyrrolizidine.

DETAILED DESCRIPTION OF THE INVENTION

The invention is conveniently illustrated by the following description of the preferred embodiments in which 1α,2α,6α,7α,7aβ-1,2,6,7-tetrahydroxypyrrolizidine (1) is synthesized from D-glycero-D-gulo-heptono-1,4-lactone (6) by two different Methods A and B, in ten steps as follows in which compound numbers in parentheses correspond to compounds shown by chemical structure herein:

A.

1) The primary hydroxyl group in heptonolactone (6) is treated with a silyl blocking agent such as tert-butyldiphenylsilyl chloride to give the protected lactone (7).

2) The protected lactone (7) is reacted with 2,2-dimethoxypropane to provide the fully protected lactone or diacetonide (9).

3) The diacetonide (9) is reacted with fluoride ion to cleave the silyl ether at C7 and thereby provide access to nitrogen in the ring and give the primary alcohol (10).

4) The primary alcohol (10) is esterified with triflic anhydride to afford the triflate (11).

5) The triflate (11) is reacted with azide ion to give the azidolactone (12).

6) The azidolactone (12) is reduced to the azidodiol (13).

7) The azidodiol (13) is reacted with methanesulfonyl chloride to provide the azidodimesylate (14).

8) The azidodimesylate (14) is catalytically hydrogenated in ethanol at ambient temperature.

9) The product from step 8 is heated in ethanol in the presence of sodium acetate to give the tetracyclic pyrrolizidine (15).

10) The acetonide groups in the tetracyclic pyrrolizidine (15) are removed by acid hydrolysis to give the product 1α,2α,6α,7α,7αβ-1,2,6,7-tetrahydroxypyrrolizidine (1).

3) The fully protected lactone or diacetonide (9) is reduced to give the silyl diol (16).

4) The silyl diol (16) is reacted with methanesulfonyl chloride to provide the dimesylate (17).

5) Nitrogen is introduced into the ring by reaction of the dimesylate (17) with benzylamine to give the monocylic pyrrolidine (20).

6) The silyl protecting group is removed from C7 of the monocylic pyrrolidine (20) by treatment with fluoride ion to provide the primary diol (21).

7) The primary diol (21) is reacted with methanesulfonyl chloride to give the unstable mesylate (22) which spontaneously closes to form the second pyrrolidine ring and give the N-benzyl pyrrolizidinium salt (23).

8) The N-benzyl group in (23) is cleaved by catalyzed hydrogenation.

9) Neutralization of the product of step 8 gives the tetracyclic pyrrolizidine (15).

10) The acetonide groups in the tetracyclic pyrrolizidine (15) are removed by acid hydrolysis to give the product 1α,2α,6α,7α,7αβ-1,2,6,7-tetrahydroxypyrrolizidine (1).

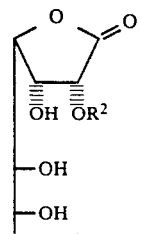

(6) R¹ = R² = H
(7) R¹ =[Si]; R² = H
(8) R¹ = R² = [Si]

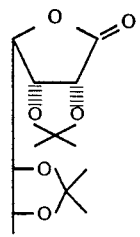

(9) R = [Si]
(10) R = H
(11) R = SO₂CF₃

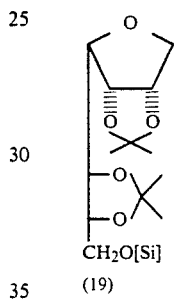

(19)

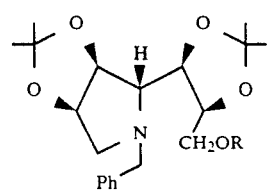

(20) R = [Si]
(21) R = H
(22) R = SO₂CH₃

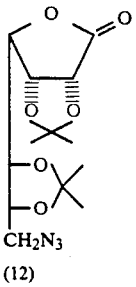

(12)

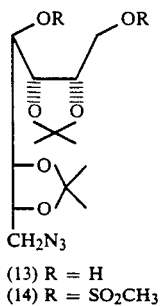

(13) R = H
(14) R = SO₂CH₃

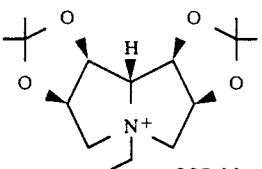

(23)

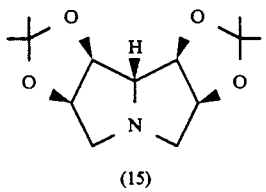

(15)

[Si] = Ph₂Buᵗ Si

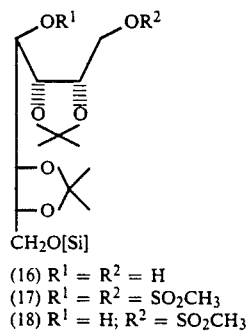

(16) R¹ = R² = H
(17) R¹ = R² = SO₂CH₃
(18) R¹ = H; R² = SO₂CH₃

B.

Steps 1 and 2 are the same as in Method A.

The fully protected lactone or diacetonide (9), namely 7-O-tert-butyldiphenylsilyl-2,3:5,6-di-O-isopropylidene-D-glycero-D-gulo-heptono-1,4-lactone, is a novel intermediate that can be used as a starting material for each of Methods A and B, above. Both Methods A and B result in preparation of the novel fully protected tetracyclic pyrrolizidine (15), namely 1α-2α,6α,-7α,7αβ-1,2,6,7-di-O-isopropylidene-1,2,6,7-tetrahydroxy pyrrolizidine, from which the protecting groups can readily be removed by acid hydrolysis.

Other such suitable reactants for use in the foregoing syntheses of Methods A and B will be apparent to the person skilled in the art after reading the present disclosure. These reactants are generally used in proportions such as to satisfy the stoichiometry of the above reaction steps. Illustrative of such other reactants are the use of t-butyldimethylsilyl chloride to introduce the silyl protecting groups; use of other ketones, e.g., acetone, 3-pentanone, dihexylketone, cyclohexanone, and the like to introduce suitable hydroxyl protecting groups; use of other azide cations to introduce the azide group, e.g. potassium, lithium and tetra-butylammonium; and use of other solvent media such as DMF, THF, DMSO, N-methylpyrrolidine, acetonitrile and the like.

The foregoing reactions in Methods A and B were illustratively carried out as follows:

SYNTHESIS OF TETRAHYDROXYPYRROLIZIDINE (1)

A. The synthesis of $1\alpha,2\alpha,6\alpha,7\alpha\beta$-1,2,6,7-tetrahydroxypyrrolizidine (1), with five adjacent chiral centres and seven adjacent carbon atoms bearing functional groups, requires the joining of C-1, C-4 and C-7 of the heptonolactone (6) by nitrogen with inversion of configuration at C-4. The order in which the formation of the different carbon-nitrogen bonds are formed is variable, although protection of the hydroxyl groups at C-2, C-3, C-5 and C-6 is required; bis-isopropylidene protection of the hydroxyl functions assists the intramolecular cyclizations to the pyrrolidine rings, since fused five-five membered rings are formed.

The primary hydroxyl group in (6) was protected as the tert-butyldiphenylsilyl ether by reaction with tert-butyldiphenylsilyl chloride in the presence of imidazole to afford (7) in 55% yield [Hanessian and Lavallee, *Can. J. Chem.* 53, 2975-2977 (1975)]. Although the silyl chloride was present in only slight excess, a significant amount (18%) of a disilyl derivative was also formed; the structure of this by-product was tentatively assigned as the 2,7-disilylether (8), since hydroxyl groups $\alpha$- to lactone carbonyl groups show enhanced reactivity in silylation reactions [Mark and Zbiral, *Monatsch. Chem.* 112, 215-239 (1981)]. Reaction with 2,2-dimethoxypropane in the presence of a catalyst of dl-camphor sulphonic acid gave the diacetonide (9) [68% yield], in which the presence of two 5-ring ketals is clearly indicated by two singlets for the quaternary isopropylidene carbons at about $\delta 110$ in the $^{13}$C NMR spectrum; the quaternary carbon of a six ring ketal generally appears below $\delta 100$. If the acetonation reaction was stopped before completion, both 5- and 6-ring monoacetonides could be isolated from the reaction mixture, indicating that (9) is the thermodynamic product.

One approach to the synthesis of (1) from the divergent intermediate (9) requires initial introduction of nitrogen at C-7. Access was gained to C-7 by cleavage of the silyl ether with fluoride ion to give the primary alcohol (10) in 86% yield. Esterification of (10) with trifluoromethane sulphonic anhydride afforded the triflate (11) which with sodium azide in dimethylformamide at room temperature gave the azide (12) [77% yield from (10)]. The lactone (12) was reduced by sodium borohydride in ethanol to the azidodiol (13) [93% yield] which was reacted with excess methanesulphonyl chloride in pyridine in the presence of 4-dimethylaminopyridine to give the dimesylate (14) [94% yield]. Hydrogenation of the azidodimesylate (14) in ethanol in the presence of a catalyst of palladium black, followed by heating in ethanol in the presence of sodium acetate, lead directly to the tetracyclic pyrrolizidine (15) in 76% yield. In (15), C-1 is equivalent with C-7, C-2 with C-6 and C-3 with C-5 giving only five signals in the $\delta 2.5$-5.0 region of the $^1$H NMR sprectrum, and only four signals in the $\delta 55$-85 region of the $^{13}$C NMR spectrum; additionally in the $^{13}$C NMR spectrum, the quaternary isopropylidene carbons are equivalent and there are two pairs of equivalent isopropylidene methyl carbons. Removal of the acetonide groups from (15) by treatment with aqueous trifluoroacetic acid gave the desired tetrahydroxypyrrolizidine (1) in 90% yield [15% overall yield for the ten steps from heptonolactone (6)]. It is clear that removal of the two cyclic ketals in (15) has resulted in a change of the torsion angles within the structure, since there are significant changes in the coupling constants between (1) and (15).

B. An alternative synthesis of (1) from the fully protected lactone (9) involves initial formation of a pyrrolidine ring between C-1 and C-4. Reduction of the lactone (9) with lithium aluminum hydride in tetrahydrofuran gave the diol (16) in the 77% yield, providing access to the C-1 and C-4 hydroxyl groups while all the other oxygen functions are protected. The silyl diol (16) was then converted into the dimesylate (17) [66% yield] by treatment with methanesulphonyl chloride in pyridine in the presence of 4-dimethylaminopyridine; the anhydrosugar (19) [32% yield] was also obtained in this reaction, presumably arising from intramolecular cyclization of the monomesylate (18). Nitrogen was introduced by reaction of the dimesylate (17) with benzylamine giving the monocyclic pyrrolidine (20) in 72% yield; efficient cyclization of 1,4-dimesylates to pyrrolidines on treatment with benzylamine has been reported by Fleet et al., *Tetrahedron* 44, 2469-2655 (1988); Fleet and Son, *Ibid.* 44, 2637-2647 (1988). The formation of the second pyrrolidine ring was achieved by first removing the silyl protecting group from C-7 of (20) by treatment with fluoride ion (84% yield). Subsequent mesylation of the primary alcohol (21) gave the unstable mesylate (22) which spontaneously closed to give the N-benzyl pyrrolizidinium salt (23). Cleavage of the N-benzyl group by hydrogenation of (23) in ethanol in the presence of palladium black, followed by neutralization with sodium bicarbonate gave the pyrrolizidine diacetonide (15) [31% yield from (21)], identical in all respects to the sample of (15) prepared by the alternative Method A, above.

GLYCOSIDASE INHIBITION

The effect of $1\alpha,2\alpha,6\alpha,7\alpha,7a\beta$-1,2,6,7-tetrahydroxypyrrolizidine (1) on the activity of 12 human liver glycosidases was tested by assay methods described by Daher et al., *Biochem. J.* 258, 613-615 (1989). The compound (1) is a weak inhibitor of all human lysosomal, Golgi II and neutral o-mannosidases ($I_{50}$ approximately 1 mM); in addition it is also a weak inhibitor of $\alpha$-fucosidase, $\alpha$- and $\beta$-galactosidase, and the broad specificity $\beta$-galactosidase/$\beta$-glucosidase. The pyrrolizidine (1) is structurally related to 1,4-dideoxy-1,4-imino-L-allitol (DIA) (24) which is also a relatively weak inhibitor of lysosomal $\alpha$-mannosidase ($K_i$ $1.2\times10^{-4}$M). DIA (24) is comparable to the pyrrolizidine (1) in its inhibition of the neutral and Golgi II $\alpha$-mannosidases [Cenci di Bello et al., *Biochem. J.* 259, 855-861 (1989)]; both DIA and (1) have a relatively broad specificity of inhibition of glycosidases [Daher et al., supra.]. In contrast, the closely related indolizidine 8,8a-diepiswainsonine (25) is a very effective inhibitor of lysosomal ($K_i$ $2\times10^{-6}$M) and Golgi processing $\alpha$-mannosidase, both in vivo and in vitro, and the indolizidine (25) fits the active site of the $\alpha$-mannosidases more closely than (1) or (24).

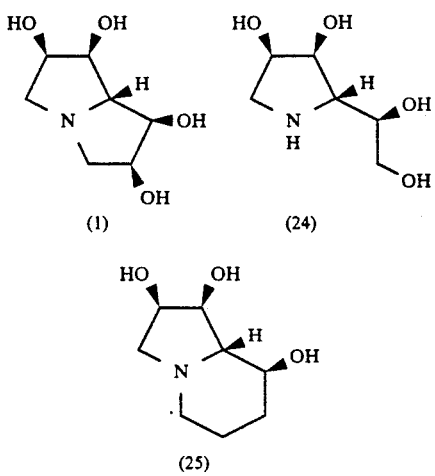

The following examples will further illustrate the invention in greater detail although it will be appreciated that the invention is not limited to these specific examples.

METHODS

Melting points were recorded on a Kofler block and are corrected. Infrared spectra were recorded on either a Perkin-Elmer 781 spectrophotometer or a Perkin-Elmer 1750 IR FT spectrometer. Optical rotations were measured on a Perkin-Elmer 241 polarimeter with a path-length of 10 cm; concentrations are given in g/100 ml. $^1$H NMR spectra were run either at 200 MHz on a Varian Gemini 200 spectrometer, or at 300 MHz on a Bruker WH 300 spectrometer. Chemical shifts are quoted on the scale using residual solvent as an internal standard. $^{13}$C NMR spectra were recorded at 50 MHz on a Varian Gemini 200 spectrometer; for samples in $D_2O$, dioxan ($\delta$ 67.2) was added as a reference. Mass spectra were recorded on either a VG Micromass ZAB 1F, a VG Mass lab 20-250 or a TRIO 1 spectrometer using chemical ionization (CI) or desorption chemical ionization (DCI) techniques. Microanalyses were performed by the microanalytical service of the Dyson Perrins Laboratory, Oxford, U.K. T.l.c. was performed on glass plates coated with silica gel Blend 41 (80% silica gel HF$_{254}$ and 20% silica gel G) or on aluminum plates coated with Merck silica gel 60F$_{254}$. Compounds were visualized with a spray of 0.2% w/v ceric sulphate and 5% ammonium molybdate in 2M sulphuric acid, or 0.5% ninhydrin in methanol (for amines). Flash chromatography was carried out using Sorbsil C60 40/60 flash silica gel. Dry column chromatography was carried out using Merck Kieselgel 60H. Ion exchange columns were packed with Aldrich 50X, 8-100 resin in the H$^+$ form Pyridine and benzylamine were distilled (and stored) over potassium hydroxide. Hexane was distilled to remove involatile fractions. Immediately prior to use, dimethylformamide (DMF) and dichloromethane were distilled from calcium hydride, and tetrahydrofurane (THF) was distilled from sodium benzophenone ketyl.

D-glycero-D-gulo-Heptono-1,4-lactone (6) was obtained from Sigma.

EXAMPLE 1

7-O-tert-Butyldiphenylsilyl-D-glycero-D-gulo-heptono-1,4-lactone (7) and 2,7-di-O-tert-Butyldiphenylsilyl-D-glycero-D-gulo-heptono-1,4-lactone (8)

D-glycero-D-gulo-Heptono-1,4-lactone (6) (10 g, 48.08 mmol) and imidazole (4.98 g, 1.5 equiv) were added to dry DMF (25 ml) and the mixture stirred at 0° C. under nitrogen. tert-Butylchlorodiphenylsilane (13.74 ml, 1.1 equiv) was added slowly, after which the reaction mixture was allowed to warm up to room temperature over three hours. After 22 hours, t.l.c. (eluant ethyl acetate) indicated that the mixture contained the desired monosilyl derivative (R$_f$ 0.65) and a smaller amount of another carbohydrate derivative (R$_f$ 0.9). The crude reaction mixture was shaken with water (50 ml), causing a white precipitate to form. Ethyl acetate (90 ml) was added and the layers separated after shaking. The aqueous layer was back-extracted with more ethyl acetate (25 ml). The combined organic extracts were washed with saturated aqueous sodium chloride (4×25 ml) and dried (magnesium sulphate). Evaporation of the solvent followed by dry column chromatography (eluant hexane ethyl: acetate, 2:1, increasing the eluant polarity with each fraction), yielding 7-O-tert-butyldiphenylsilyl-D-glycero-D-gulo-heptono-1,4-lactone (7) (11.02 g, 55%) as a white solid, m.p. 54°-57° C. (Found: C, 61.58; H, 6.86%. $C_{23}H_{30}O_7Si$ requires: C, 61.87; H, 6.77%); $[\alpha]_d^{20}$ −10.56° (c, 0.99 in CHCl$_3$); $\nu_{max}$ (CHCl$_3$) 3410 (broad, OH) and 1790 cm$^{-1}$ ($\gamma$-lactone); and 2,7-di-O-tert-butyldiphenylsilyl-D-glycero-D-gulo-heptono-1,4-lactone (8) (5.94 g, 18%) as a colorless, viscous oil $[\alpha]_D^{20}$ −4.08° (c, 1.20 in CHCl$_3$); $\nu_{max}$ (CHCl$_3$) 3440 (broad, OH) and 1790 cm$^{-1}$ ($\gamma$-lactone).

EXAMPLE 2

7-O-tert-Butyldiphenylsilyl-2,3:5,6-di-O-isopropylidene-D-glycero-D-gulo-heptono-1,4-lactone (9)

7-O-tert-Butyldiphenylsilyl-d-glycero-D-gulo-heptono-1,4-lactone (7) (3.00 g, 6.73 mmol) and dl-camphor sulphonic acid (0.15 g, 5%) were dissolved in dry acetone (60 ml). 2,2-Dimethoxypropane (3.50 g, 5 equiv) was added and the mixture was stirred at 50° C. under reflux for 22 hours. The reaction was quenched by addition of excess sodium hydrogen carbonate, at which stage t.l.c. (eluant hexane:ethyl acetate, 6:1) indicated that the reaction mixture contained three compounds, one major product (R$_f$ 0.6) together with two minor products (R$_f$ 0.8 and 0.1). After filtration and evaporation of the solvent, the residue was purified by flash chromatography (eluant hexane:ethyl acetate, 8:1), yielding 7-O-tert-butyldiphenylsilyl-2,3:5,6-di-O-isopropylidene-D-glycero-D-gulo-heptono-1,4-lactone (9) (2.40 g, 68%) as a white, crystalline solid, m.p. 104°-106° C. (Found: C, 66.19; H, 7.58%. $C_{29}H_{38}O_7Si$ requires: C, 66.1%; H, 7.27%); $[\alpha]_D^{20}$ −21.64° (c, 0.98 in CHCl$_3$); $\nu_{max}$ (CHCl$_3$) 1790 ($\gamma$-lactone). 1386 and 1377 cm$^{-1}$ (CMe$_2$).

EXAMPLE 3

2,3:5,6-Di-isopropylidene-D-glycero-D-gulo-heptono-1,4-lactone (10)

7-O-tert-Butyldiphenylsilyl-2,3:5,6-di-O-isopropylidene-D-glycero-D-gulo-heptono-1,4-lactone (9) (4.11 g, 7.81 mmol) was dissolved in dry THF (200 ml) and the solution was stirred under nitrogen. Tetra-n-butylammonium fluoride (11.7 ml of a 1M solution in THF, 1.5 equiv) was added dropwise. After one and a half hours t.l.c. (eluant hexane:ethyl acetate, 6:1) indicated one product at the baseline but no starting material ($R_f$ 0.6). Evaporation of the solvent gave a pale yellow oil which was purified by flash chromatography (eluant ethyl acetate:hexane, 3:2) yielding 2,3:5,6-di-O-isopropylidene-D-glycero-D-gulo-heptono-1,4-lactone (10) (1.93 g, 86%) as a white, crystalline solid, m.p. 115°–120° C. (Found: C, 54.46; H, 6.99%. $C_{13}H_{20}O_7$ requires: C, 54.16; H, 6.99%); $[\alpha]_D^{20}$ −53.40° (c, 1.05 in $CHCl_3$); $\nu_{max}$ ($CHCl_3$) 3560 (OH), 1790 ($\gamma$-lactone), 1388 and 1379 cm$^{-1}$ ($CMe_2$).

EXAMPLE 4

7-Azido-7-deoxy-2,3:5,6-di-O-isopropylidene-D-glycero-D-gulo-heptono-1,4-lactone (12)

2,3:5,6-Di-O-isopropylidene-D-glycero-D-gulo-heptono-1,4-lactone (10) (0.50 g, 1.74 mmol) was dissolved in dry dichloromethane (50 ml) and dry pyridine (0.28 ml, 2 equiv) was added and the solution was stirred at −30° C. under nitrogen. Trifluoromethanesulphonic anhydride (0.44 ml, 1.5 equiv) was added slowly, and after 30 minutes, t.l.c. (eluant ethyl acetate:hexane, 2:1) indicated complete conversion to product ($R_f$ 0.9). The reaction mixture was worked up as quickly as possible by washing with ice cold saturated aqueous sodium chloride (35 ml) followed by drying over sodium sulphate. The solvent was evaporated leaving an orange residue which was dissolved in dry DMF (20 ml). Without further purification, sodium azide (0.226 g, 2 equiv based on quantitative triflation) was added and the mixture stirred at room temperature under nitrogen. After 30 minutes, t.l.c. (eluant hexane:ethyl acetate, 2:1) indicated that a product had formed ($R_f$ 0.4). The solvent was evaporated, leaving a residue which was dissolved in dichloromethane (30 ml) and washed with water (3×15 ml). After drying (magnesium sulphate) and evaporation of the solvent, flash chromatography (eluant hexane:ethyl acetate, 2:1) yielded 7-azido-7-deoxy-2,3:5,6-di-O-isopropylidene-D-glycero-D-gulo-heptono-1,4-lactone (12) (0.42 g, 77% over two steps) as a white, crystalline solid, m.p. 89°–91° C. (Found: C, 50.10; H, 6.29; N, 13.18%. $C_{13}H_{19}N_3O_6$ requires: C, 49.84; H, 6.11; N, 13.41%); $[\alpha]_d^{20}$ +34.57° (c, 1.00 in $CHCl_3$); $\nu_{max}$ ($CHCl_3$) 2110 ($N_3$), 1795 ($\gamma$-lactone), 1386 and 1378 cm$^{-1}$ ($CMe_2$).

EXAMPLE 5

7-Azido-7-deoxy-2,3:5,6-di-O-isopropylidene-D-glycero-D-gulo-heptitol (13)

7-Azido-7-deoxy-2,3:5,6-di-O-isopropylidene-D-glycero-D-gulo-heptono-1,4-lactone (12) (1.84 g, 5.88 mmol) was dissolved in ethanol (100 ml) and stirred at 0° C. under nitrogen. Sodium borohydride (0.445 g, 2 equiv) was added and the reaction mixture allowed to warm up to room temperature. After 18 hours, t.l.c. (eluant hexane:ethyl acetate, 2:1) indicated that all starting material had been converted to product ($R_f$ 0.2). The reaction was quenched by addition of excess solid ammonium chloride, with effervescence. Filtration and evaporation of the solvent gave a residue which was purified by flash chromatography (eluant hexane:ethyl acetate, 2:1) yielding 7-azido-7-deoxy-2,3:5,6-di-O-isopropylidene-D-glycero-D-gulo-heptitol (13) (1.74 g, 93%) as a colorless, viscous oil (Found: C, 49.26; H, 7.30; N, 3.26%. $C_{13}H_{23}N_3O_6$ requires: C, 49.20; H, 7.30; N, $[\alpha]_D^{20+}$ +2.87° (c, 0.94 in $CHCl_3$); $\nu_{max}$ 3553 (broad, OH), 2107 ($N_3$), 1384 and 1375 cm$^{-1}$ ($CMe_2$).

EXAMPLE 6

7-Azido-7-deoxy-2,3:5,6-di-O-isopropylidene-1,4-di-O-methanesulphonyl-D-glycero-D-gulo-heptitol (14)

7-Azido-7-deoxy-2,3:5,6-di-O-isopropylidene-D-glycero-D-gulo-heptitol (13) (0.95 g, 3.00 mmol) and 4-dimethylaminopyridine (DMAP) (1 mg) were dissolved in dry pyridine (15 ml) and stirred at 0° C. under nitrogen. Methanesulphonyl chloride (1.39 ml, 6 equiv) was added slowly and after 4 hours the reaction mixture was allowed to warm up to room temperature. After 18 hours, t.l.c. (eluant hexane: ethyl acetate, 2:1) indicated that no starting material remained ($R_f$ 0.2) while a major product had formed ($R_f$ 0.25). The solvent was evaporated, leaving a red oil which was dissolved in ethyl acetate (150 ml) and washed with water (75 ml). After drying (magnesium sulphate) the crude mixture was purified by flash chromatography (eluant hexane: ethyl acetate, 2:1) yielding 7-azido-7-deoxy-2,3:5,6-di-O-isopropylidene-1,4-di-O-methanesulphonyl-D-glycero-D-gulo-heptitol (14) (1.33 g, 94%) as a colorless, viscous oil, $[\alpha]_D^{20}$ +8.22° (c, 1.07 in $CHCl_3$); $\nu_{max}$ ($CHCl_3$) 2109 cm$^{-1}$ ($N_3$).

EXAMPLE 7

1$\alpha$,6$\alpha$,7$\alpha$,7$\alpha\beta$-1,2:6,7-Di-O-isopropylidene-1,2,6,7-tetrahydroxy pyrrolizidine (15)

7-Azido-7-deoxy-2,3:5,6-di-O-isopropylidene-1,4-di-O-methane sulphonyl-D-glycero-D-gulo-heptitol (14) (0.64 g, 1.35 mmol) was dissolved in ethanol (50 ml) and palladium black (10%) was added. After degassing the solution, the reaction mixture was stirred vigorously under hydrogen at room temperature for two hours. At this stage, t.l.c. (eluant hexane:ethyl acetate, 2:1) indicated that all starting material ($R_f$ 0.25) had reacted to give a product which remained at the baseline. The reaction mixture was filtered through celite to remove the catalyst, sodium acetate (0.33 g, 3 equiv based on quantitative reduction) added and the mixture stirred at 50° C. under nitrogen. After 12 hours, t.l.c. (eluant ethyl acetate:methanol, 9:1) showed that the reaction mixture was predominantly one compound ($R_f$ 0.5). After evaporating the solvent, the crude mixture was purified by flash chromatography (eluant ethyl acetate, increasing polarity to ethyl acetate:methanol, 9:1) giving 1$\alpha$,2$\alpha$,6$\alpha$,7$\alpha$,7$\alpha\beta$-1,2:6,7-di-O-isopropylidene-1,2,6,7-tetrahydroxy pyrrolizidine (15) (0.26 g, 76% over two steps) as a pale brown solid, m.p. 66°–69° C. (diethyl ether) (Found: C, 60.81; H, 8.44; N, 5.23%. $C_{13}H_{21}NO_4$ requires: C, 61.16; H, 8.29; N, 5.49%); $[\alpha]_D^{20}$ +1.06° (c, 1.14 in $CHCl_3$).

EXAMPLE 8

1$\alpha$,2$\alpha$,6$\alpha$,7$\alpha$,7$\alpha\beta$-1,2,6,7-Tetrahydroxy Pyrrolizidine (1)

1$\alpha$,2$\alpha$,6$\alpha$,7$\alpha$,7$\alpha\beta$-1,2:6,7-Di-O-isopropylidene-1,2,6,7-tetrahydroxy pyrrolizidine (15) (112 mg, 0.44 mmol) was dissolved in 50% aqueous trifluoroacetic acid (20 ml) and stirred at room temperature for six hours. After evaporation of the solvent, the residue was dissolved in water and purified on an ion exchange column (H$^+$ form), eluting with 0.5M aqueous ammonia. Freeze drying yielded 1$\alpha$,2$\alpha$,6$\alpha$,7$\alpha$,7$\alpha\beta$-1,2,6,7-tetrahydroxy pyrrolizidine (1) (69 mg, 90%) as a pale brown solid, m.p. 170°–175° C. (dec.) (Found: C, 47.62; H, 7.65; N, 7.77%. $C_7H_{13}NO_4$ requires: C, 47.99; H, 7.48; N, 8.00%); $[\alpha]_D^{20}$ 0° (c, 1.06 in $H_2O$); $\nu_{max}$ (KBr disc) 3400 cm$^{-1}$ (very broad, OH).

EXAMPLE 9

7-O-tert-Butyldiphenylsilyl-2,3:5,6-di-O-isopropylidene-D-glycero-D-gulo-heptitol (16)

7-O-tert-Butyldiphenylsilyl-1,2:5,6-di-O-isopropylidene-D-glycero-D-gulo-heptono-1,4-lactone (9) (116 mg, 0.22 mmol) was dissolved in dry THF (10 ml) and stirred at 0° C. under nitrogen. Lithium aluminum hydride (25 mg, 3 equiv) was added and the reaction mixture allowed to warm up slowly to room temperature. After 9 hours, t.l.c. (eluant hexane:ethyl acetate, 2:1) indicated that no starting material remained ($R_f$ 0.9) while a major product had formed ($R_f$ 0.1). The reaction was quenched by the addition of excess solid ammonium chloride, the mixture filtered and the solvent evaporated. Purification by flash chromatography (eluant hexane:ethyl acetate, 3:1) yielded 7-O-tert-butyldiphenylsilyl-2,3:5,6-di-O-isopropylidene-D-glycero-D-gulo-heptitol (16) (78 mg, 77%) as a colorless, viscous oil, $[\alpha]_D^{20}$ −2.39° (c, 1.05 in CHCl$_3$); $\nu_{max}$ (CHCl$_3$) 3561 (broad, OH), 1383 and 1374 cm$^{-1}$ (CMe$_2$).

EXAMPLE 10

7-O-tert-Butyldiphenylsilyl-2,3:5,6-di-O-isopropylidene-1,4-di-O-methanesulphonyl-D-glycero-D-guloheptitol (17) and 1,4-anhydro-7-O-tert-butyldiphenylsilyl-1-deoxy-2,3:5,6-di-O-isopropylidene-D-glycero-D-gulo-heptitol (19)

7-O-tert-Butyldiphenylsilyl-2,3:5,6-di-O-isopropylidene-D-glycero-D-gulo-heptitol (16) (260 mg, 0.49 mmol) and DMAP (1 mg) were dissolved in dry pyridine (10 ml) and stirred at 0° C. under nitrogen. Methanesulphonyl chloride (0.15 ml, 4 equiv) was added slowly and after 3 hours the reaction mixture was allowed to warm up to room temperature. After 20 hours, t.l.c. (eluant hexane:ethyl acetate, 3:2) indicated that two products had formed ($R_f$ 0.5 and 0.8) while no starting material remained ($R_f$ 0.4). After evaporation of the solvent, the residue was shaken with ethyl acetate (60 ml), leaving an insoluble brown solid. The filtrate was washed with water (70 ml) and dried (magnesium sulphate). After filtration and evaporation of the solvent, flash chromatography (eluant hexane:ethyl acetate, 3:1) yielded 7-O-tert-butyldiphenylsilyl-2,3:5,6-di-O-isopropylidene-1,4-di-O-methane sulphonyl D-glycero-D-gulo-heptitol (17) (224 mg, 67%) as a colorless, viscous oil, $[\alpha]_D^{20}$ −9.40° (c, 1.08 in CHCl$_3$); and 1,4-anhydro7-O-tert-butyldiphenylsilyl-1-deoxy-2,3:5,6-di-O-isopropylidene-D-glycero-D-gulo-heptitol (19) (81 mg, 32%) as a colorless, viscous oil, $[\alpha]_D^{20}$+34.71° (c, 1.02 in CHCl$_3$); $\nu_{max}$ (CHCl$_3$) 1382 and 1375 cm$^{-1}$ (CMe$_2$).

EXAMPLE 11

N-Benzyl-7-O-tert-butylphenylsilyl-1,4-dideoxy-2,3:5,6-di-O-isopropylidene-1,4-imino-D-glycero-D-allo-heptitol (20)

7-O-tert-Butyldiphenylsilyl-2,3:5,6-di-O-isopropylidene-1,4-di-O-methanesulphonyl-D-glycero-D-gulo-heptitol (17) (147 mg, 0.21 mmol) was dissolved in benzylamine (10 ml) and stirred at 50° C. under nitrogen for 72 hours. At this stage, t.l.c. (eluant hexane:ethyl acetate, 3:1) indicated that no starting material remained ($R_f$ 0.2) while a major product had formed ($R_f$ 0.8). The benzylamine was evaporated, leaving a dark red oil which was dissolved in ethyl acetate (20 ml). Silica gel was added and the solvent evaporated to pre-adsorb the compound. Flash chromatography (eluant hexane, increasing polarity to hexane:ethyl acetate, 6:1) yielded N-benzyl-7-O-tert-butyldiphenylsilyl-1,4-dideoxy-2,3:5,6-di-O-isopropylidene-1,4-imino-D-glycero-D-allo-heptitol (20) (94 mg, 72%) as a pale yellow, viscous oil, $[\alpha]_D^{20}$ −14.08° (c, 1.20 in CHCl$_3$); $\nu_{max}$ (CHCl$_3$) 1383 and 1375 cm$^{-1}$ (CMe$_2$).

EXAMPLE 12

N-Benzyl-1,4-dideoxy-2,3:5,6-di-O-isopropylidene-1,4-imino-D-glycero-D-allo-heptitol (21)

N-Benzyl-7-O-tert-butyldiphenylsilyl-1,4-dideoxy-2,3:5,6-di-O-isopropylidene-1,4-imino-D-glycero-D-allo-heptitol (20) (94 mg, 0.16 mmol) was dissolved in dry THF (10 ml) and stirred at room temperature under nitrogen. Tetra-n-butylammonium fluoride (0.23 ml of a 1M solution in THF, 1.5 equiv) was added and after 3 hours, t.l.c. (eluant hexane:ethyl acetate, 3:1) indicated that no starting material remained ($R_f$ 0.8) while a major product had formed ($R_f$ 0.25). Evaporation of the solvent followed by flash chromatography (eluant hexane:ethyl acetate, 3:1) yielding N-benzyl-1,4-dideoxy-2,3:5,6-di-O-isopropylidene-1,4-imino-D-glycero-D-allo-heptitol (21) (48 mg, 84%) as a colorless, viscous oil, $[\alpha]_D^{20}$−58.44° (c, 1.03 in CHCl$_3$); $\nu_{max}$ (CHCl$_3$) 3670 (OH), 1386 and 1377 cm$^{-1}$ (CMe$_2$).

EXAMPLE 13

1α,2α,6α,7α,7αβ-1,2:6,7-Di-O-isopropylidene-1,2,6,7-tetrahydroxy pyrrolizidine 15)

N-Benzyl-1,4-dideoxy-2,3:5,6-di-O-isopropylidene-1,4-imino-D-glycero-D-allo-heptitol (21) (91 mg, 0.25 mmol) was dissolved in dry dichloromethane (15 ml). Dry pyridine (0.04 ml, 2 equiv) was added and the solution stirred at 0° C. under nitrogen. Methanesulphonyl chloride (0.03 ml, 1.5 equiv) was added slowly, and after 4 hours the reaction mixture was allowed to warm up to room temperature. After 24 hours, t.l.c. (eluant hexane:ethyl acetate, 3:1) indicated a product at the baseline but no starting material ($R_f$ 0.25). Evaporation of the solvent and trituration with diethyl ether (2×5 ml) gave a white solid residue which was dissolved in ethanol (5 ml) and added to a mixture of pre-reduced palladium black (10%) in degassed ethanol (10 ml). The resultant mixture was stirred vigorously at room temperature under hydrogen for 24 hours and then filtered through celite. Evaporation of the solvent gave a white solid residue which was dissolved in ethyl acetate (20 ml), washed with saturated aqueous sodium hydrogen carbonate (10 ml) and dried (magnesium sulphate). Flash chromatography (eluant ethyl acetate, increasing polarity to ethyl acetate:methanol, 9:1) yielded 1α,2α,6α,7α,7αβ-1,2:6,7-di-O-isopropylidene-1,2,6,7-tetrahydroxy pyrrolizidine (15) (20 mg, 31%) as a pale yellow oil with spectroscopic data identical to those in Example 7, above.

Various other examples will be apparent to the person skilled in the art after reading the present disclosure without departing from the spirit and scope of the invention. It is intended that all such other examples be included within the scope of the appended claims.

What is claimed is:

1. A method for the production of 1α,2α,6α,7α,7αβ-1,2,6,7-tetrahydroxypyrrolizidine comprising:
   a) reacting D-glycerol-D-gulo-heptono-1,4-lactone with a silyl blocking agent to protect the primary hydroxyl group and give a protected lactone,
   b) reacting the protected lactone with 2,2-dimethoxypropane to provide a fully protected lactone,
   c) reducing the fully protected lactone to give a silyl diol,
   d) reacting the silyl diol with methanesulfonyl chloride to provide a dimesylate,
   e) reacting the dimesylate with benzylamine to introduce nitrogen into the ring and give a monocyclic pyrrolidine,
   f) reacting the monocyclic pyrrolidine with fluoride ion to remove the silyl protecting group and provide a primary diol,
   g) reacting the primary diol with methanesulfonyl chloride to give a mesylate which spontaneously closes to form a second pyrrolidine ring and give a N-benzyl pyrrolizidinium salt,
   h) cleaving the N-benzyl group in the N-benzyl pyrrolizidinium salt by catalytic hydrogenation,
   i) neutralizing the resulting product to give a tetracyclic pyrrolizidine, and
   j) removing the acetonide protecting groups of the tetracyclic pyrrolizidine by acid hydrolysis to give 1α,2α,6α,7α,7αβ-1,2,6,7-tetrahydroxypyrrolizidine.

* * * * *